(12) United States Patent
Borkowski (10) Patent No.: US 6,188,570 B1
(45) Date of Patent: Feb. 13, 2001

(54) PORTABLE DRUG INFORMATION COMPUTER

(76) Inventor: Brian Borkowski, 349 Walkley Hill Rd., Haddam, CT (US) 06438

( * ) Notice: Under 35 U.S.C. 154(b), the term of this patent shall be extended for 0 days.

(21) Appl. No.: 09/503,895

(22) Filed: Feb. 15, 2000

Related U.S. Application Data (63) Continuation of application No. 08/999,792, filed on Sep. 22, 1997, now Pat. No. 6,025,984.

(51) Int. Cl.[7] .................... G06F 1/16; H05K 5/00
(52) U.S. Cl. .............. 361/683; 361/679; 364/708.1; 364/209.01; 364/709.12; 283/900; 707/1
(58) Field of Search ................ 361/683, 680–682, 361/679; 364/708.1, 700, 709.01, 709.09, 709.12, 716.01, 716.02; 283/900; 707/1, 100

(56) References Cited

U.S. PATENT DOCUMENTS

| | | | |
|---|---|---|---|
| 4,289,958 | 9/1981 | Thomas | 235/489 |
| 4,553,958 * | 11/1985 | LeCocq | 604/67 |
| 4,660,991 * | 4/1987 | Simon | 368/10 |
| 4,686,624 * | 8/1987 | Blum et al. | 364/415 |
| 4,709,331 * | 11/1987 | Barkett et al. | 364/413 |
| 4,766,542 | 8/1988 | Pilarczyk | 364/413 |
| 4,807,170 * | 2/1989 | Kulli et al. | 364/413.01 |
| 4,858,207 * | 8/1989 | Buchner | 368/10 |
| 4,962,491 * | 10/1990 | Schaeffer | 368/21 |
| 5,004,270 | 4/1991 | Schaul et al. | 283/48.1 |
| 5,020,037 * | 5/1991 | Raven | 368/10 |
| 5,041,086 * | 8/1991 | Koenig et al. | 604/65 |
| 5,099,463 * | 3/1992 | Lloyd et al. | 368/10 |
| 5,181,743 | 1/1993 | Lloyd | 283/48.1 |
| 5,200,891 * | 4/1993 | Kehr et al. | 364/413.01 |
| 5,289,157 * | 2/1994 | Rudick et al. | 340/309.15 |
| 5,299,121 | 3/1994 | Brills et al. | 364/413.01 |
| 5,358,280 | 10/1994 | Scales | 283/63 |

(List continued on next page.)

FOREIGN PATENT DOCUMENTS

| | | | |
|---|---|---|---|
| 9-51922 * | 2/1997 | (JP) | A61G/12/00 |
| 9-117490 * | 5/1997 | (JP) | A61J/3/00 |

Primary Examiner—Leo P. Picard
Assistant Examiner—Anatoly Vortman
(74) Attorney, Agent, or Firm—Darby & Darby (57) ABSTRACT

A portable drug information computer (10) having a housing (12) which has a housing top (12T), a housing bottom (12B), a housing right side (12R), a housing left side (12L), a housing front (12F), and a housing back (12A). The portable drug information computer (10) further has a battery (16) contained within the housing (12) and a microchip (20) positioned within the housing (12). The microchip (20) has a memory storage means having drug name and drug information contained therein selected from a group consisting of indications, actions, pharmokinetics, contra indications & precautions, adverse reactions, route & dosage, availability, time action, nursing & medical implications, and drug interactions. The portable drug information computer (10) further has at least one functional button positioned within the housing front (12F) and electrically connected to the microchip (20). The at least one functional button is selected from a group consisting of indications button (22), actions button (24), pharmokinetics button (26), contra indications & precautions button (28), adverse reactions button (30), route & dosage button (32), availability button (34), time-action button (36), nursing & medical implications button (36), and a drug interactions button (40). The portable drug information computer (10) further has an alphanumeric keyboard (42), a space bar (44), a backspace button (46), an enter button (50), at least one directional button, and a display (14) positioned within the housing front (12F) and electricity connected to the microchip (20) containing computer software (110) contained therein.

14 Claims, 4 Drawing Sheets

U.S. PATENT DOCUMENTS

| | | | |
|---|---|---|---|
| 5,382,232 * | 1/1995 | Hague et al. | 604/65 |
| 5,390,238 | 2/1995 | Kirk et al. | 379/93 |
| 5,401,059 | 3/1995 | Ferrario | 283/67 |
| 5,408,443 * | 4/1995 | Weinberger | 368/10 |
| 5,456,663 | 10/1995 | Lemelson | 604/50 |
| 5,555,157 | 9/1996 | Moller et al. | 361/683 |
| 5,597,995 | 1/1997 | Williams et al. | 235/375 |
| 5,623,390 | 4/1997 | Noda et al. | 361/679 |
| 5,640,297 | 6/1997 | Labaze | 361/683 |
| 5,661,632 | 8/1997 | Register | 361/683 |
| 5,675,524 | 10/1997 | Bernard | 364/705.05 |
| 5,694,289 | 12/1997 | Ema | 361/680 |
| 5,713,856 * | 2/1998 | Eggers et al. | 604/65 |
| 5,734,883 | 3/1998 | Umen et al. | 395/601 |
| 5,742,476 | 4/1998 | Miyazaki et al. | 361/683 |
| 5,772,635 * | 6/1998 | Dastur et al. | 604/131 |
| 5,786,983 | 7/1998 | Brenner et al. | 361/680 |
| 5,796,575 | 8/1998 | Podwalny et al. | 361/681 |
| 5,915,971 * | 6/1999 | Ramsay et al. | 434/276 |
| 6,025,984 | 2/2000 | Borkowski | 361/679 |

* cited by examiner fig. 1 fig. 2

PORTABLE DRUG INFORMATION COMPUTER

This is a continuation of application Ser. No. 08/999,792, filed Sep. 22, 1997 now U.S. Pat. No. 6,025,984. Each of these prior applications is hereby incorporated herein by reference, in its entirety.

BACKGROUND OF THE INVENTION

1. Field of the Invention

The present invention relates to drug information computers. More particularly, the present invention relates to portable drug information computers having a microchip containing software and drug information for easy retrieval

2. Description of the Prior Art

Nurses are required by the state and the hospital to know, at least, about the indications and actions of the drugs they are administering. With patients who have up to twenty drugs or more, time becomes a critical factor in delivering care, and the present invention allows rapid access to drug information compared to the time lost while using paper drug guides.

Numerous innovations for drug information computer have been provided in the prior art that are described as follows. Even though these innovations may be suitable for the specific individual purposes to which the address, they differ from the present invention as hereinafter contrasted.

In U.S. Pat. No. 4,289,958, titled System for Identifying Solid Dosage Units, invented by Stephen Thomas, a system is described for identifying solid dosage units, such as tablets or capsules, of drugs or other medications which may be found beside a patient or which may have been handed in at a hospital. The system comprises a sizing member having a substantially straight sided channel which tapers towards one end to define a V-shaped channel in which a dosage unit can be placed, markings being associated with the channel for indicating a dimension parameter of the unit when so placed. The system also comprises a color region having a plurality of colored areas for indicating a color parameter of the dosage unit, a shape region bearing a series of shape parameters and an information storage and retrieval system which may be in the form of a punched card system or a computer. Parameters of the dosage unit obtained from said V-shaped channel, from said color region and from said shape region, and, optionally, from other physical characteristics of the dosage unit are fed into the information storage and retrieval system to provide an identification of the unit.

The patented invention differs from the present invention because the patented invention is a manual device system for identifying solid dosage units of tablets or capsules which may be found beside a patient or which 1494 have been handed in at a hospital. The patent invention is a mechanical device which indicates a dosage based on the size of a pill or capsule.

In U.S. Pat. No. 4,766,542, titled System and Software for Pharmaceutical Prescription Compliance, invented by Richard R. Pilarczyk, a system for contacting customers of a pharmacy automatically to remind them that their prescriptions need to be refilled does so using a computer, memory, and automatic telephone dialing and by voice synthesizing equipment. Information concerning each customer and his or her prescription is placed in a database in the memory. A schedule file which lists customer name, phone number, the drug prescribed and refill due date is created from this information. The schedule file is kept in chronological order by refill due date. At selected times, customers whose prescriptions are due to be refilled within selected time periods are automatically contacted by the computer using the automatic telephone dialer. When the telephone is answered, the voice synthesizer identifies the customer by name, the proscribed drug and prescription number. The voice synthesizer then reminds the customer that the prescription is due to be refilled if the medication was taken as prescribed. The system generates various reports for the pharmacist concerning its automatic activities.

The patented invention differs from the present invention because the patented invention is a system for contacting customers of a pharmacy, automatically, to remind them that their prescriptions need to be refilled. The patented invention does so using a computer, memory, and automatic telephone dialing and voice synthesizing equipment. The patented invention lacks a feature for displaying information about the drug being prescribed. Your invention is a computerized drug data base which can be stored on a Palm Top Computer device having: a data input device such as a disk, card or CD drive, keyboard, and processing unit. The data base of drug information is stored on a data storage device such as a disk, card, or CD. A computer software program operating on the palm top computer provides access to the drug information data base and provides features which facilitate accessing specific information related to treatment, dispensing and patient care.

In U.S. Pat. No. 4,916,441, titled Portable Handheld Terminal, invented by Peter P Gombrich, a handheld pocket terminal (22) having a display screen (40) and bar code reader (42).

The patented invention differs from the present invention because the patented invention is a device and system which reads bar codes and dispenses drugs according to the information on the bar code. The patented invention lacks features similar to the present invention.

In U.S. Pat. No. 5,299,121, titled Non-Prescription Drug Medication Screening System, invented by Albert R. Brill and Denis Sosnoski, a system for use in pharmacies which uses customer inputs to assist the customer with the selection of an appropriate non-prescription medication to relieve symptoms of an illness, injury or the like. The system uses an expert system to perform the selection. The system utilizes a personal computer with a keyboard, monitor and disk drive as input/output devices with appropriate programming for prompting a user to input information which is used by a knowledge base to determine non-prescription medications which may be purchased by the customer to relieve symptoms of injuries and illnesses covered by the knowledge base. The system operates by prompting a user, typically a customer, in a pharmacy to input basic customer information . After the basic customer information has been input the customer is prompted to select one main symptom category from a list of displayed and the choice made results in the appropriate knowledge base being loaded for the next step. The logic of the loaded knowledge base itself determines which questions are asked of the customer by the display of appropriate questions on the monitor. The output of each knowledge base on completion of the questions and answers is a list of component medications recommended for use with the symptoms described. The list of component medications generated by the execution of the knowledge base is used to search a database to find the appropriate product to be recommended.

The patented invention differs from the present invention because the patented invention is a system for use in pharmacies which uses customer inputs to assist the customer with the selection of an appropriate non-prescription medication. The patented invention is limited to non prescription drugs. The patented invention is a software program designed to operate on a PC. The present invention is a computerized drug data base including both prescription and nonprescription drugs, which can be stored on a Palm Top Computer device having: a data input device such as a disk, card or CD drive, keyboard, and processing unit. The data base of drug information is stored on a data storage device such as a card, CD, or disk. A computer software program operating on the palm top computer provides access to the drug information data base and provides features which facilitate accessing specific information related to treatment, dispensing and patient care.

In U.S. Pat. No. 5,004,270, titled Buying Guide, invented by Malcolm Schaul and James Broderick, a novel buying guide means detachably secured to a newspaper or magazine insert is provided. The multi-page buying guide includes check list with indicators to note and organize an inventory of shopping items and coupons from the accompanying newspaper or insert. Redeemable coupons for use in conjunction with the buying guide are provided in the accompanying insert. The buying guide further includes pouch means within the guide for coupons representing products indicated on the guide. Indicators are printed adjacent selected products to notify the buyer that coupons related to particular items on the checklist are located in the accompanying insert.

The patented invention differs from the present invention because the patented invention is a novel buying guide newspaper or magazine insert. The patented invention is a manual system for making a list of shopping items. The patented invention lacks features similar to the present invention.

In U.S. Pat. No. 5,390,238, titled Health Support System, invented by Dan M. Kirk, Norman C. Gehring and George J. Butorac, a home health and communications support system and method which includes at least one health support unit for monitoring and supporting a patient, at least one monitoring terminal, and a network server coupled between at least one health support unit and at least one monitoring terminal for exchanging information between at least one health support unit and at least one monitoring terminal. The health support unit comprises a medication controller, communications module for interacting with the patient, central data processor, and external communications interface. The central data processor stores and manipulates patient data generated by the medication controller and by the communications module for patient interaction. The external communications interface allows access to patient data and accepts external data from an external source.

The patented invention differs from the present invention because the patented invention is a home health and communications support system and method. The patented invention lacks a data base of information on drugs. The present invention is a computerized drug data base which can be stored on a Palm Top Computer device. A computer software program operating on the palm top computer provides access to the drug information data base and provides features which facilitate accessing specific information related to treatment, dispensing and patient care.

In U.S. Pat. No. 5,456,663, titled Drugs and Methods for Treating Disease, invented by Jerome H. Lemelson, a method for treating a disease and drug units for use in performing such method. The method involves invading and flooding select cells of a living being with a drug or medical material to correct a genetic flaw, destroy or otherwise prevent the production or multiplication of a disease defining substance such as a virus in such cells or prevent the cells from uncontrollably growing or dividing. The method involves injecting or otherwise administering a dose of drug units to the body or bloodstream of a living being and targeting such drug units to the select cells to be treated and invaded with the drug of the units. In a preferred form, the drug is a derivative of vitamin A, such as 13-cis retinoic acid or other synthetic retinoid, which operates upon invading and flooding immature or precancerous white blood cells to restore the regulatory apparatus which they lack permitting them to mature normally and perform their normal functions such as their formation of platelets and preventing them from multiplying uncontrollably. The method involves forming such drug units of a small quantity of such drug, preferably encapsulated in a microcapsule or biodegradable material and containing one or more targeting particles attached thereto for targeting or attaching the drug unit to the desired immature or diseased cell to be treated with the drug upon its attachment and release to the select cell to which the drug unit targets. In a particular form, select doses of such drug units are intermittently administered to the body or bloodstream by timed controlled administration of such select dose and/or by their timed release from a body implant employing biodegradation or other mechanism to effect such timed does or drug unit release. In another form, the implant contains or is connected to a computer and includes means for detecting the presence and quantity or level of the cells requiring treatment, wherein the computer effects and controls the release of select quantities of such targeting drug units to the body or bloodstream in accordance with the information computed by the computer.

The patented invention differs from the present invention because the patented invention is a method for invading and flooding selected cells of a living being with a drug or medical material to correct a genetic flaw, destroy or otherwise prevent the production or multiplication of a disease defining substance or prevent the cells from uncontrollably growing or dividing. The patented invention lacks features similar to the present invention.

In U.S. Pat. No. 5,597,995, titled Automated Medical Prescription fulfillment system having Work Stations for Imaging, Filling, and Checking the Dispensed Drug Product, invented by Jeffrey P. Williams, Robert Mathews and Alvin Towle, the patented invention provides a pharmacy system for automating the medical prescription fulfillment process for a customer. It includes an imaging work station having a host computer for receiving data entry of an original medical prescription for a prescribed drug product and customer information and for producing a prescription transaction data record; and electronic communication device for communicating the prescription transaction data record from the host computer to a series of computers. A filling work station includes dispensing apparatus for counting, dispensing and packaging of the dispensed drug product into the drug vial for the customer. A checking work station includes a scanner for scanning the bar code label on the drug vial, and a display for displaying the digitized image of the original medical prescription, and for displaying a digitized image of the prescribed drug product to allow a first visual comparison between the digitized image of the prescribed drug product and the dispensed drug product in the drug vial, and a second visual comparison between the digitized image of the original medical prescription and the dispensed drug product in the drug vial before it is given to the customer.

The patented invention differs from the present invention because the patented invention provides a pharmacy system for automating the medical prescription fulfillment process for a customer. The patented invention is much more complex than your invention and has features such automated dispensing of prescription drugs. The patented invention lacks features similar to the present invention.

In U.S. Pat. No. 5,358,280, titled Apparatus for Assembling and Displaying Information, invented by Thomas C. Scales, a group of cards containing printed information on one or more selected topics and interconnected to form a deck of such cards. The deck may include a title card bearing indicia denoting a particular topic of information on other cards in the deck, and also may include one or more cards containing general information on the topic, as well as subject cards containing information on one or more specific items relating to the topic. The subject cards include indicia, preferably along a marginal portion of the card, denoting the particular subject for which that card, or the facing surface of the card, contains information.

The patented invention differs from the present invention because the patented invention is a group of cards with which the user manually locates printed information on one or more selected topics. The patented invention lacks features similar to the present invention.

In U.S. Pat. No. 5,401,059, titled Process and Unit for Univocal Pairing of Drugs Corresponding to a Prescribed Treatment with a Given Patient, invented by Angelo Ferrario, a process and apparatus are disclosed for pairing drugs corresponding to a prescribed treatment with a given patient including marking of arm bands or other identification devices with the patient's identification data, permanently attaching the identification device to the patient, retrieving a drug corresponding to the prescribed treatment and verifying its agreement with the drug administration data stored on the identification device, introducing the drug into a container which is previously marked with the patient identification data and drug administration data and closing the container. The process further includes moving the container to a drug delivery station at the patient location and verifying agreement of the data marked on the container with that stored on the identification device of the patient. Subsequently, the container is opened and agreement between the patient identification data marked on the identification device and the drug administration data marked on the container are verified with the drug subsequently being administered upon verification of the agreement.

The patented invention differs from the present invention because the patented invention is a process and apparatus are disclosed for pairing drugs corresponding to a prescribed treatment with a given patient. The patented invention is an automated tracking, dispensing, and verifying machine for: providing a patient with drug treatment on a scheduled basis. The present invention is a portable drug information data base which lists information about specific drugs in a format tailored for the medical community.

In U.S. Pat. No. 5,181,743, titled Drug Information Request System, invented by Christopher Lloyd, the present invention relates to a system whereby a consumer, and in particular a patient, may make a request that information with respect to a drug be transmitted to him or her. In accordance with the present invention, a doctor may provide a patient with an information request post card. The information request post card may, in one aspect, for example, have a first information correlation component and a second postal destination component. The first component may comprise a plurality or correlation groups, each correlation group comprising a said identification symbol and an associated check-off section for being marked so as to designate the said identification symbol, and a consumer identification section for the insertion of postal information of a consumer. The second component may have a destination information section comprising postal information of a distant site from which information about a drug associated with a designated identification symbol may be transmitted to a consumer using postal information present in said consumer identification section.

The patented invention differs from the present invention because the patented invention is a manual means for determining information about a drug. The patented invention functions with a postcard which is mailed by a user to a central location where information about the prescribed drugs are located and sent to the users by return mail. The patented invention lacks features similar to the present invention.

Numerous innovations for drug information computers have been provided in the prior art that are adapted to be used. Even though these innovations may be suitable for the specific individual purposes to which they address, they would not be suitable for the purposes of the present invention as heretofore described.

SUMMARY OF THE INVENTION

The present invention is a pocket/hand size computer drug guide that allows someone to enter a word that is searched and defined. The present invention allows a user to enter a drug name and to find out information about the drug. Once the user types in a drug name, they could push enter, which provides proper spelling. If the spelling of the word was incorrect, the computer provides a list, which is scrollable up or down, for the best matching drug name. Once the drug is selected, such as Zantac or Cyclobenzaprine, the user may optionally push additional buttons to find information on indications of the drug, its action, pharmacokinetics (which would include, absorption, distribution, metabolism and excretion, and half life), contra indications and precautions, adverse reaction and side effects, route and dosage, availability, and time/action profile. The present invention can be geared towards nurses and doctors separately or together by including two extra categories for nursing implications and medical implications.

It is very unlikely that someone would buy the present invention if it could not be updated as new information on drugs is released. Therefore, the present invention includes an interchangeable disc (or via modem) that could be bought every year that would include the most up-to-date information on medications. These discs could be as easy to change as someone changing cartridges/games on a Nintendo (TM) Game Boy.

The present invention also includes cross reference for drag interactions. This means that the someone could check to see if a group of drugs ordered for a patient would interact with each other.

The computer is much quicker to use and lighter to carry than a paper drug book.

The computer eliminates nurses in hospitals having to buy several drug books because of incomplete information or because the books quickly loose pages as they are used numerous times daily.

The computer would promote medication learning as students and professionals would be more apt to use the computer drug guide that the paperback drug guide because it is easy to use and quicker to access drug information.

It is appealing and perhaps popular with computer technology of today to nursing students who are required to each have their own drug book(s).

It is appealing to nursing students in clinical settings who are required to write information of their patient's medications on note cards. The note cards are to be carried with them while providing care for patients. This can be very tedious and allows room for errors when the cards contain incomplete information.

Doctors appreciate the lighter, more efficient, and more economical way to retrieve information than carrying books on them.

The disc for upgrading would hopefully be cheaper than buying a new paperback drug guide every year.

Possible cross reference for drug interactions would provide valuable information to nurses and especially medical students and residents who are beginning to write medication orders for patients.

The types of problems encountered in the prior art are books are too cumbersome and a quick reference guide does not contain enough information.

In the prior art, unsuccessful attempts to solve this problem were attempted namely: computer programs which are maintained on large desk top computer. However, the problem was solved by the present invention because it is portable.

Innovations within the prior art are rapidly being exploited in the field of drug information services.

The present invention went contrary to the teaching of the art which teaches published books and large computer programs maintained on cumbersome hardware.

The present invention solved a long felt need for a portable drug guide computer.

The present invention produced unexpected results namely: lowered doctor's and nurse's malpractice insurance.

A synergistic effect was produced utilizing the present invention due to the following facts and results from experimentation: when two or more drugs are entered simultaneously, the computer programs displays of any known side effects or adverse reactions will occur.

Accordingly, it is an object of the present invention to provide a portable drug information computer which comprises a housing, display, battery, ON/OFF switch, modem, microchip, functional buttons, alphanumeric keyboard, space bar, and directional buttons.

More particularly, it is an object of the present invention to provide a housing which comprises a housing top, a housing bottom, a housing right side, a housing left side, a housing front, and a housing back.

In keeping with these objects, and with others which will become apparent hereinafter, one feature of the present invention resides, briefly stated, in a housing back further comprises a housing back access door.

When the battery is designed in accordance with the present invention, it further comprises a power means port.

In accordance with another feature of the present invention, the modem further comprises a modem jack.

Another feature of the present invention is that the functional buttons comprise indications button, actions button, pharmokinetics button, contra indications & precautions button, adverse reactions button, route & dosage button, availability button, time-action button, nursing & medical implications button, drug interactions button, backspace button, clear button, and enter button.

Still another feature of the present invention is that the directional buttons comprise UP arrow button, DOWN arrow button, LEFT arrow button, and RIGHT arrow button.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings.

BRIEF LIST OF REFERENCE NUMERALS UTILIZED IN THE DRAWING

10—portable drug information computer (10)
12—housing (12)
12T—housing top (12T)
12B—housing bottom (12B)
12R—housing right side (12R)
12L—housing left side (12L)
12F—housing front (121)
12A—housing back (12A)
12AA—housing back acccss door (12AA)
14—display (14)
16—battery (16)
16A—power means port (16A)
17—ON/OFF switch (17)
18—modem (18)
18A—modem jack (18A)
20—microchip (20)
22—indications button (22)
24—actions button (24)
26—pharmokinetics button (26)
28—contra indications & precautions button (28)
30—adverse reactions button (30)
32—route & dosage button (32)
34—availability button (34)
36—time-action button (36)
38—nursing & medical implications button (38)
40—drug interactions button (40)
42—alphanumeric keyboard (42)
44—space bar (44)
46—backspace button (46)
48—clear button (48)
50—enter button (50)
52A—UP arrow button (52A)
52B—DOWN arrow button (52B)
52C—LEFT arrow button (52C)
52D—RIGHT arrow button (52D)

DESCRIPTION OF THE PREFERRED EMBODIMENT

Figure 1:
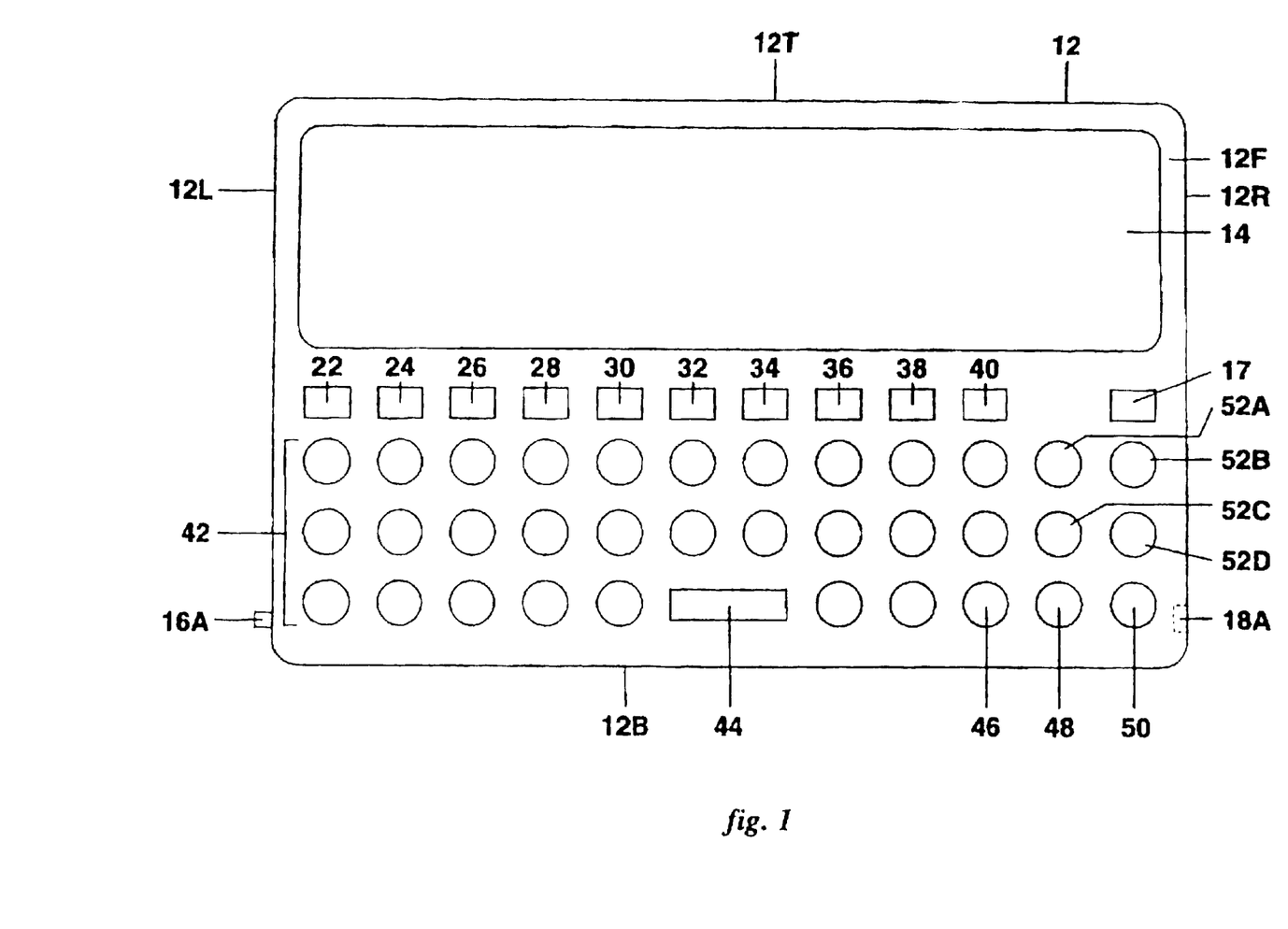
FIG. 1 is a front view of a portable drug information computer.

Firstly, referring to FIG. 1 is a front view of a portable drug information computer (10) which comprises a housing (12) which comprises a housing top (12T), a housing bottom (12B), a housing right side (12R), a housing left side (12L), a housing front (12F), and a housing back (12A). The portable drug information computer (10) further comprises a battery (16) contained within the housing (12). The battery (16) is preferably a rechargeable NiCad battery but optionally may be an alkaline battery. Solar power may also be utilizied as a power means. The housing (12) further comprises a power means port (16A) having open access thereto, the power means port (16A) is electrically connected to the battery (16). The power means port (16A) functions as a connection to a recharging means. The portable drug information computer (10) may optionally further comprises a modem (18) electrically connected to the microchip (20) and to a modem jack (18A) contained within the housing (12) having open access thereto. The modem (18) allows updating of drug information into the storage means.

The portable drug information computer (10) further comprises a microchip (20) positioned within the housing (12). The microchip (20) comprises a memory storage means having drug name and drug information contained therein selected from a group consisting of indications, actions, pharmokinetics, contra indications & precautions, adverse reactions, route & dosage, availability, time action, nursing & medical implications, and drug interactions. The memory storage means may be RAM, CACHE, a floppy drive, a hard drive, a CD Rom drive, and/or Tape drive.

The portable drug information computer (10) further comprises an ON/OFF switch (17) positioned within the housing (12) and electrically connected between the battery (16) and the microchip (20).

The portable drug information computer (10) further comprises at least one functional button positioned within the housing front (12F) and electrically connected to the microchip (20). The at least one functional button is selected from a group consisting of indications button (22), actions button (24), pharmokinetics button (26), contra indications & precautions button (28), adverse reactions button (30), route & dosage button (32), availability button (34), time-action button (36), nursing & medical implications button (36), and a drug interactions button (40). When the functional button is activated an electronic signal is sent to the microchip which in turn retrieves the corresponding drug information from the storage means.

The portable drug information computer (10) further comprises an alphanumeric keyboard (42) positioned within the housing front (12F) and electrically connected to the microchip (20). The user keys in the drug name into the portable drug information computer (10) utilizing the alphanumeric keyboard (42).

The portable drug information computer (10) further comprises a space bar (44) positioned within the housing front (12F) and electrically connected to the microchip (20). The space bar (44) functions to add a space between words or letters.

The portable drug information computer (10) further comprises a backspace button (46) positioned within the housing front (12F) and electrically connected to the microchip (20). The backspace button (46) functions to delete a previous letter or number entered.

The portable drug information computer (10) further comprises an cater button (50) positioned within the housing front (12F) and electrically connected to the microchip (20). The enter button (50) functions to send the typed drug name to the microchip (20).

The portable drug information computer (10) may optionally comprise a clear button (48) positioned within the housing front (12F) and electrically connected to the microchip (20). The clear button (48) functions to remove previous drug information from the display (14) allowing input of a new drug name.

The portable drug information computer (10) further comprises at least one directional button positioned within the housing front (12F) and electrically connected to the microchip (20). The at least one directional button is selected from a group consisting of UP arrow button (52A), DOWN arrow button (5213), LEFT arrow button (52C), and RIGHT arrow button (52D). The directional button functions to move a cursor to a position on the display (14).

The portable drug information computer (10) further comprises a display (14) positioned within the housing front (12F) and electrically connected to the microchip (20). The display (14) may be an active matrix or LCD.

Figure 2:
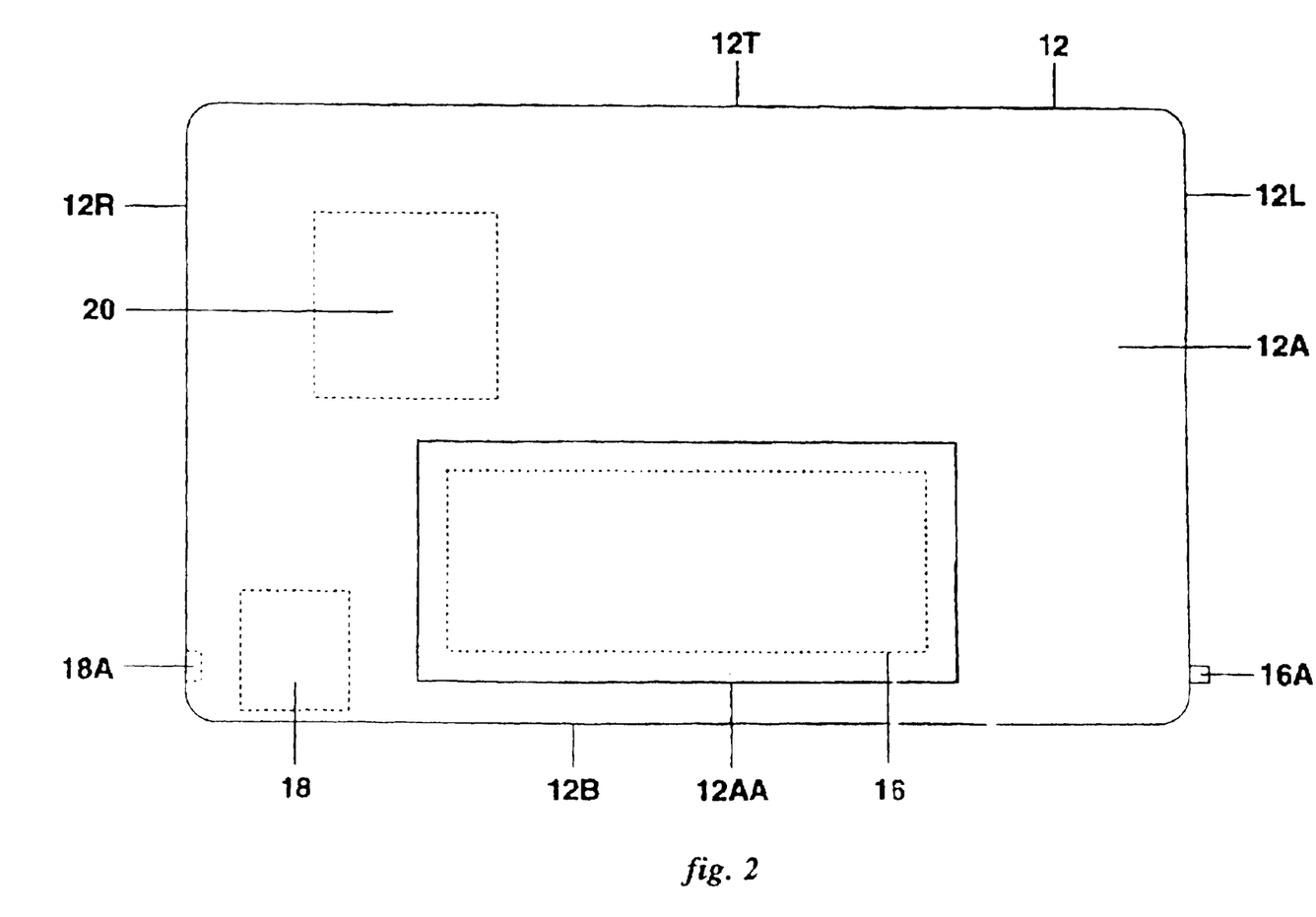
FIG. 2 is a back view of a portable drug information computer.

Referring to FIG. 2 is a back view of a portable drug information computer (10). The housing back (12A) comprises a housing back access door (12AA) which functions to allow the user to maintain (or replace) the battery (16) positioned within the housing (12).

Figure 3:
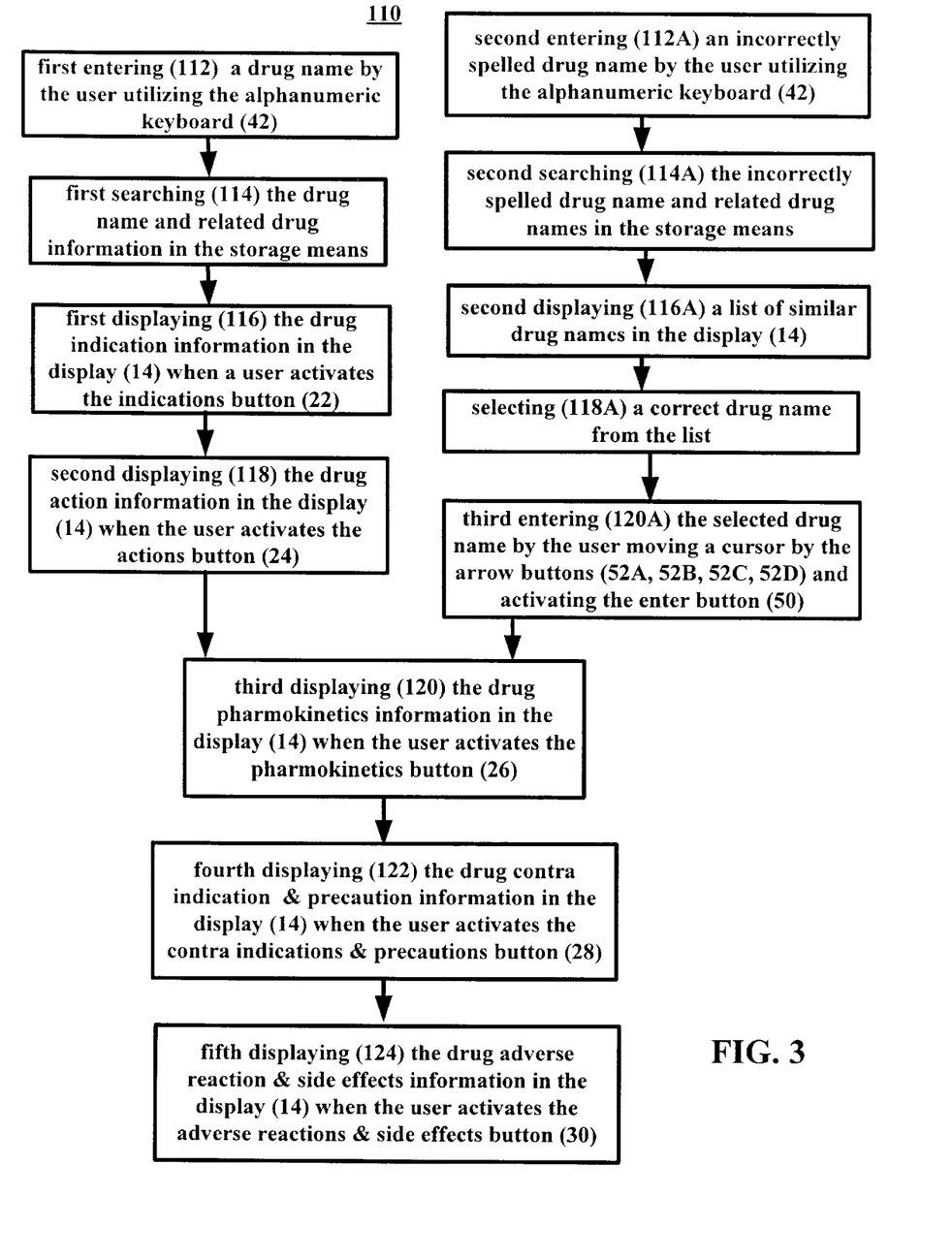
FIG. 3 is a diagrammatic representation of computer software contained within the microchip.
Figure 4:
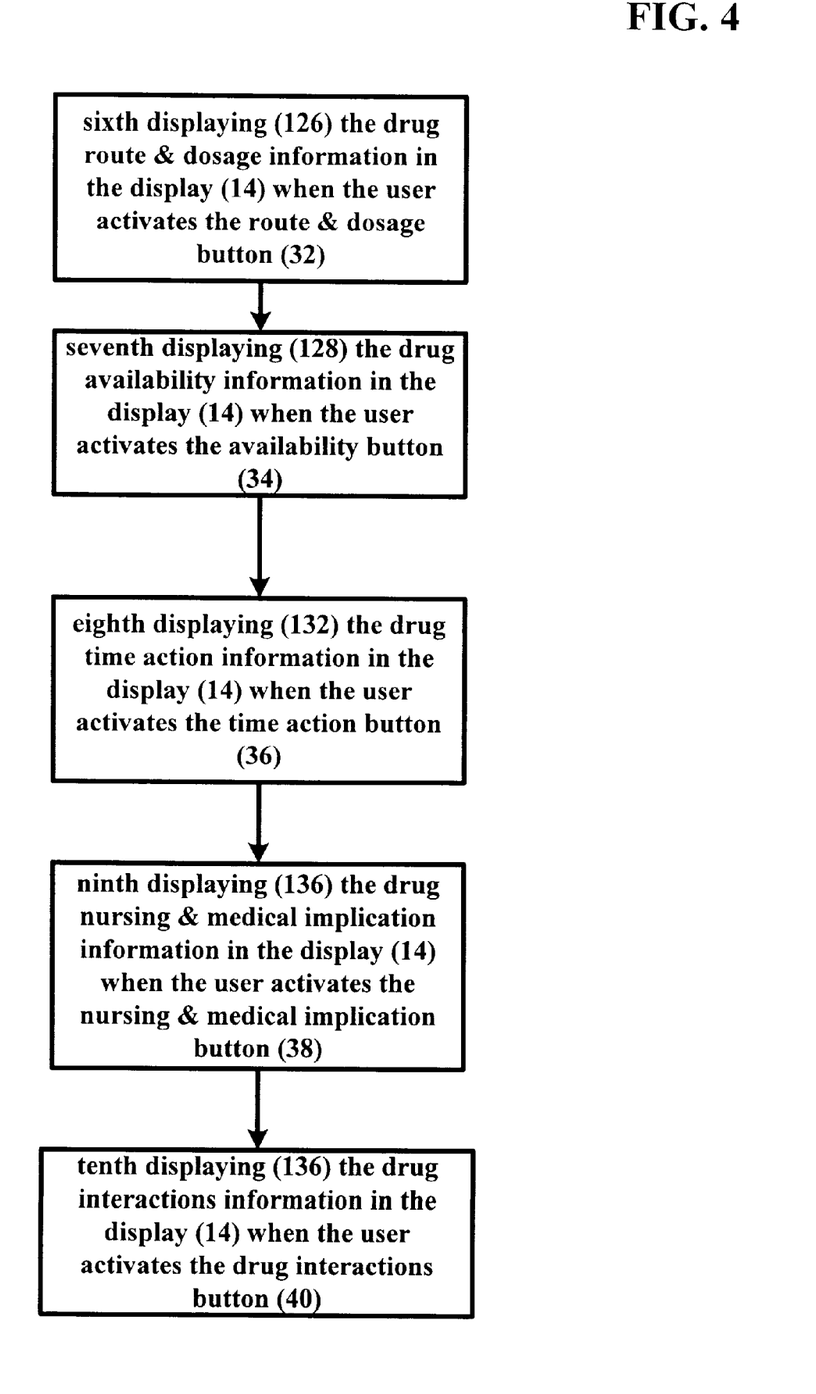
FIG. 4 is a diagrammatic representation of computer software contained within the microchip as a continuation of FIG. 3.

Now referring to FIG. 3 which is a diagrammatic representation of computer software contained within the microchip (20). Referring to FIG. 4 which is a diagrammatic representation of computer software contained within the microchip (20) as a continuation of FIG. 3.

The portable drug information computer (10) further comprises computer software (110) contained within the microchip (20). The computer software (110) consisting of the following steps:

i) first entering (112) a drug name by the user utilizing the alphanumeric keyboard (42), ii) first searching (114) the drug name and related drug information in the storage means, ii) first displaying (116) the drug indication information in the display (14) when a user activates the indications button (22), iv) second displaying (118) the drug action information in the display (14) when the user activates the actions button (24), v) third displaying (120) the drug pharmokinetic information in the display (14) when the user activates the pharmokinetics button (26), vi) fourth displaying (122) the drug contra indication & precaution information in the display (14) when the user activates the contra indications & precautions button (28), vii) fifth displaying (124) the drug adverse reaction information in the display (14) when the user activates the adverse reactions button (30), viii) sixth displaying (126) the drug route & dosage information in the display (14) when the user activates the route & dosage button (32), ix) seventh displaying (128) the drug availability information in the display (14) when the user activates the availability button (34), x) eighth displaying (130) the drug availability information in the display (14) when the user activates the availability button (34), xi) ninth displaying (132) the drug time action information in the display (14) when the user activates the time-action button (36), xii) tenth displaying (134) the drug nursing & medical implication information in the display (14) when the user activates the nursing & medical implications button (38), and xiii) eleventh displaying (136) the drug nursing & medical implication information in the display (14) when the user activates the drug interactions button (40).

If the user enters the incorrect drug name, the portable drug information computer (10) further consists of the following steps:

A) second entering (112A) an incorrectly spelled drug name by the user utilizing the alphanumeric keyboard (42);

B) second searching (114A) the incorrectly spelled drug name and related drug names in the storage means;

C) second displaying (116A) a list of similar drug names in the display (14);

D) selecting (118A) a correct drug name from the list; and

E) third entering (120A) the selected drug name by the user moving a cursor by the arrow buttons (52A, 52B, 52C, 52D) and activating the enter button (50).

It will be understood that each of the elements described above, or two or more together, may also find a useful application in other types of constructions differing from the type described above.

While the invention has been illustrated and described as embodied in a drug information computer, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

What is claimed is:

1. A portable drug information computer, comprising:

A) a housing;

B) a microchip positioned within the housing, the microchip comprising a memory storage means for storing a drug name and drug information contained therein, said drug name and drug information including an indications, actions, pharmokinetics, contra indications, adverse reactions & side effects, route & dosage, availability, time-action, nursing and medical implications, and drug interactions;

C) a plurality of functional buttons supported by the housing and electrically connected to the microchip, said plurality of functional buttons comprising an indications button, time-actions button, pharmokinetics button, contraindications & precautions button, adverse reactions and side effects button, route & dosage button, availability button, time-action button, nursing & medical implications button, and a drug interactions button; and D) a display supported by the housing and electrically connected to the microchip.

2. The portable drug information computer as in claim 1, further comprising an ON/OFF switch positioned within the housing and electrically connected between a battery and the microchip.

3. The portable drug information computer as in claim 1, further comprising a modem communicatively connected to the microchip for providing updated drug information to the memory storage means.

4. The portable drug information computer as in claim 3, wherein the modem is connected to a modem jack which is accessible at the housing.

5. The portable drug information computer as in claim 1, further comprising a keyboard supported by the housing and electrically connected to the microchip.

6. The portable drug information computer as in claim 5, wherein the keyboard includes keys selected from the group of: alphanumeric keys, a space bar, a backspace button, an enter button, and directional buttons.

7. The portable drug information computer as in claim 1, wherein the drug name and drug information comprise a database, and wherein means database s stored on one of a disk, card or CD.

8. A portable drug information computer, comprising:

A) a housing;

B) a microchip positioned within the housing;

C) a memory storage means communicatively connected to the microchip for storing a drug name and drug information contained therein, the drug name and drug information including, for each drug, indications, actions, pharmokinetics, contra indications, adverse reactions & side effects, route & dosage, availability, time-action, nursing and medical implications, and drug interactions;

D) at least three functional buttons supported by the housing and electrically connected to the microchip, the functional buttons being selected from the group consisting of: an indications button, time-actions button, pharmokinetics button, contraindications & precautions button, adverse reactions and side effects button, route & dosage button, availability button, time-action button, nursing & medical implications button, and a drugs interactions button;

E) a keyboard supported by the housing and electrically connected to the microchip for inputting a selected drug name; and E) a display supported by the housing and electrically connected to the microchip, wherein said at least one functional button, when pressed, provides an electronic signal to the microchip causing said microchip to retrieve drug information concerning the selected drug name from the memory storage means and to present the retrieved information on the display.

9. The portable drug information computer as in claim 8, further comprising an ON/OFF switch positioned within the housing and electrically connected between a battery and the microchip.

10. The portable drug information computer as in claim 8, further comprising a modem communicatively connected to the microchip for providing updated drug information to the memory storage means.

11. The portable drug information computer as in claim 10, wherein the modem is connected to a modem jack which is accessible at the housing.

12. The portable drug information computer as in claim 8, wherein the keyboard includes keys selected from the group of: alphanumeric keys, a space bar, a backspace button, an enter button, and directional buttons.

13. The portable drug information computer as in claim 8, wherein the drug name and drug information comprise a database, and wherein means database is stored on one of a disk, card or CD.

14. The portable drug information computer as in claim 8, wherein the at least one functional button is a drug interactions button, wherein plural drug names are inputted to select plural drug names, and wherein the retrieved information presented on the display includes any known side effects or adverse reactions for the plural selected drug names.

* * * * *